(12) United States Patent
Hiromoto

(10) Patent No.: US 7,897,154 B2
(45) Date of Patent: Mar. 1, 2011

(54) DERMAL DROPS

(75) Inventor: Bryan Hiromoto, Puunene, HI (US)

(73) Assignee: ABR, LLC, Puunene, HI (US)

( * ) Notice: Subject to any disclaimer, the term of this patent is extended or adjusted under 35 U.S.C. 154(b) by 704 days.

(21) Appl. No.: 11/836,375

(22) Filed: Aug. 9, 2007

(65) Prior Publication Data

US 2008/0107677 A1    May 8, 2008

Related U.S. Application Data

(60) Provisional application No. 60/837,159, filed on Aug. 10, 2006.

(51) Int. Cl.
*A61K 36/06*    (2006.01)
*A61K 9/00*    (2006.01)
*A61K 47/00*    (2006.01)

(52) U.S. Cl. .................. 424/195.15; 424/400; 424/439

(58) Field of Classification Search ........................ None
See application file for complete search history.

(56) References Cited

U.S. PATENT DOCUMENTS

| | | | |
|---|---|---|---|
| 5,643,884 A | 7/1997 | Anderson et al. | |
| 6,943,007 B2 * | 9/2005 | Yoo et al. | ............... 435/254.1 |
| 2004/0092014 A1 | 5/2004 | Hiromoto | |
| 2005/0238655 A1 | 10/2005 | Stamets | |

FOREIGN PATENT DOCUMENTS

WO    WO-2004/006643    1/2004

OTHER PUBLICATIONS

Agrawal et al., Blackwell-Synergy-Eco Letters (2002) 5:377-385.
Alquini et al., FEMS Microbiol. Let. (2004) 230:47-52.
An, ed., *Handbook of Industrial Mycology* (2005) 22:75-77.
Chang et al., Mycologist (1992) 6:64-65.
Haridas et al., PNAS (2001) 98:5821-5826.
Huang et al., Basic and Clinical Pharmacology and Toxicology (2005) 96:3-14.
Kang et al., Life Sci. (2006) 78(6):607-613 (Epub: Aug. 19, 2005).
Leon et al., J. Nat. Prod. (2004) 67:2008-2011.
Li et al., J. Ethnopharmacol (2004) 92:1-21.
Lindequist et al., eCAM (2005) 2:285-289.
Mancheno et al., Acta Crystallogr. Sect. D. Biol. Crystal. (2004) 60:1139-1141.
Miura et al., Mol. Pharmacol. (1999) 56:1324-1328.
Sato et al., Biol. Pharmaceut. Bull. (2002) 25:81-86.
Tateno et al., J. Biol. Chem. (2003) 278:40455-40463.
Tomasi et al., Pharmazie (2004) 59:290-293.
Yoshikawa et al., Chem. Pharm. Bull. (2001) 49:327-329.
Zamuner et al., J. Braz. Chem. Soc. (2005) 16(4):863-867.
International Search Report and Written Opinion for PCT/US07/75645, mailed Mar. 12, 2008, 5 pages.

* cited by examiner

*Primary Examiner*—Christopher R Tate
*Assistant Examiner*—Randall Winston
(74) *Attorney, Agent, or Firm*—Morrison & Foerster LLP

(57) ABSTRACT

Dermal drops that, when applied topically to animal subjects, can ameliorate symptoms of conditions such as diabetes and Parkinson's disease are prepared as concentrates of the culture filtrate of a *Basidiomycete* fungus grown under appropriate conditions. The concentrate can also be used as a convenient source of liquid compost factor.

11 Claims, 1 Drawing Sheet

DERMAL DROPS

RELATED APPLICATION

This application claims priority from U.S. provisional application 60/837,159 filed 10 Aug. 2006. The contents of this document are incorporated herein by reference.

TECHNICAL FIELD

The invention relates to methods and formulations for topical application of concentrated fungal culture filtrates that are beneficial for a variety of chronic conditions, and to diluted forms of such concentrates useful as growth stimulants in agriculture.

BACKGROUND ART

The growing popularity of alternative approaches to conditions such as diabetes, inflammation, cancers, and neurological diseases using herbal extracts or other natural products in lieu of synthetic pharmaceuticals has focused attention on the possibility of deriving useful compositions from a variety of sources. A large number of biologically active compounds are present in fungi. For example, the *Handbook of Industrial Mycology*, An, Z., ed. (2005) 22:75-77 notes the presence of an insulin mimic in *Pseudomassaria* sp and anticancer and antiulcer agent in *Aspergillus*.

Mushrooms—i.e., macrofungi that have a distinctive fruiting body large enough to be seen with the naked eye and picked by hand (Lindequist, U., et al., *eCAM* (2005) 2:285-289 quoting Chang, S. T., et al., *Mycologist* (1992) 6:64-65)—are also sources for useful compounds. The Lindequist article is a review entitled "The Pharmacological Potential of Mushrooms" and mentions that mushrooms are mainly of the genus *Basidiomycete*, although some species of *Ascomycetes* belong to mushrooms.

The review article by Lindequist discloses that there are a number of antibacterial and antifungal mushrooms, antiviral mushrooms, antitumor mushrooms, mushrooms that are immunomodulators, components that have antitumor activity, cytostatic activity, antiallergic activity, antiatherogenic activity and hypoglycemic activity as well as activities that are anti--inflammatory and hepatoprotective. Specific compounds contained in certain mushrooms have been identified and are described in this article.

There has also been considerable interest in herbal medicines that contain peroxisome proliferator-activated receptor (PPAR) modulators. Among these compounds is dehydrotrametenolic acid. This is a triterpenoid of the formula

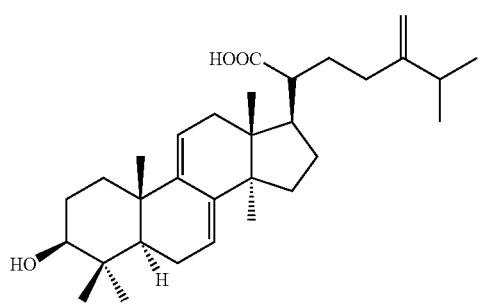

Dehydrotrametenolic acid (DHTA)

DHTA is known to occur in mushrooms as disclosed by Li, W. L., et al., *J. Ethnopharmacol* (2004) 92:1-21.

Lanostane triterpenes have also been found in mushrooms, including *Basidiomycetes* as disclosed by Zamuner, M. L. M., et al., *J. Braz. Chem. Soc.* (2005) 16:1-9. Various biologically active compounds from the fungus *Laetiporus sulphureus* have also been described by Yoshikawa, K., et al., *Chem. Pharm. Bull.* (2001) 49:327-329. These include a benzofuran glycoside and a $C_{10}$ acetylenic acid. Methanolic extracts from *Basidiomycete* mushrooms have been shown to be cytotoxic to murine cancer cell lines by Tomasi, S., et al., *Pharmazie* (2004) 59:290-293.

U.S. Pat. No. 5,643,884 to Glycomed describes a specific triterpenoid derivatives that have a multiplicity of medicament properties.

These modulators are considered to treat various disorders including hyperlipidemia as described by Huang, T. H.-W., et al., *Basic and Clinical Pharmacology and Toxicology* (2005) 96:3-14. These compounds are also reported to protect hepatic cells against the cytotoxicity of cadmium by Miura, N., et al., *Mol. Pharmacol.* (1999) 56:1324-1328.

Dehydrotrametenolic acid (DHTA) is also reported to induce pre-adipocyte differentiation and sensitize animal models of non-insulin-dependent diabetes to insulin by Sato, M., et al., *Biol. Pharmaceut. Bull.* (2002) 25:81-86. DHTA also is reported to inhibit the growth of *H. ras* so as to induce apoptosis in transformed rat2 cells by Kang, H. M., et al., *Life Sci.* (2005) August 18th. DHTA is found in several polypores including *Laetiporus sulphureus*. Other triterpenoids have also been shown to induce apoptosis as disclosed in Haridas, V., et al., *PNAS* (2001) 98:5821-5826.

Other reports have indicated that triterpenes from *L. sulphureus* may induce apoptosis in HL60 human myeloid leukemia cells (León, F., et al., *J. Nat. Prod.* (2004) 67:2008-2011. Other compounds from *L. sulphureus* include hemolytic lectins Mancheno, J., et al., *Acta Crystallogr.* Sect. D. Biol. Crystal. (2004) 60:1139-1141, Tateno, H., et al., *J. Biol. Chem.* (2003) 278:40455-40463. Various saccharides and glycosides have also been isolated from this fungus (Alquini, G., et al., *FEMS Microbiol. Let.* (2004) 230:47-52, Yoshikawa, K., et al., *Chem. Pharm. Bull.* (Tokyo) (2001) 49:327-329. Triterpenes are also known to be components of the natural defense systems of plants against herbivores and pathogens. Some of the triterpene defense compounds are produced naturally by plants, for example, as disclosed by Agrawal, A. A., et al., *Blackwell-Synergy-Eco Letters* (2002) 5:377-385.

In addition, U.S. patent publication 2005/0238655 describes antiviral properties of extracts of certain *Polyporus* fungi, especially with respect to orthopox virus. The antiviral compounds are apparently prepared by extraction from the mycelium rather than obtained from culture filtrate.

It has now been found that when *Basidiomycetes* are cultured under suitable conditions, the concentrated filtered culture medium can be applied directly to the skin in small quantities and is able to effect amelioration of symptoms of a variety of chronic conditions including pain, fatigue, diabetes and neurological disorders, and to effect treatment of certain tumors. In addition, the concentrate may be diluted to increase crop yields and induce systemic acquired resistance in plants. The concentrate represents an efficient way to supply a composition that has the effects of liquid compost factor as disclosed in PCT publication WO 2004/006643.

DISCLOSURE OF THE INVENTION

The invention is generally directed to methods to treat undesirable chronic or endogenous conditions in human and veterinary subjects by applying to the skin of the subject a concentrated filtrate of the culture medium of a *Basidiomycete* fungus, which fungus has been cultured under conditions which promote the formation of compounds with therapeutic activity as well as penetrants that ease the transfer of active compounds including proteins across dermal and cellular barriers. Because of this latter property, the concentrated filtrate may be applied topically and the beneficial compounds absorbed directly into the system from the skin. The concentrated filtrate may also be used in conjunction with other therapeutic materials whose transport into cells is desired. The invention is also directed to the use of concentrate to supply an economic form of liquid compost factor for assisting plant growth.

Thus, in one aspect, the invention is directed to a concentrate prepared from the culture filtrate of a *Basidiomycete* fungus, where the culture filtrate is the liquid portion of the culture, however harvested, wherein the culture has been maintained for at least a year, and wherein the medium has a BRIX value of 5-16, and contains 0.01-0.7% potassium ion and sufficient carotenoid to impart a yellow, orange or red color and wherein the culture is maintained in the substantial absence of agitation and in the presence of long wavelength light. The soluble proteins in the culture filtrate are removed by denaturation and the remaining liquid portion is concentrated at a temperature below boiling to a BRIX value of at least 20. The concentrate itself, or, optionally, the concentrate supplemented with additional small amounts of mushroom extract can be used topically to relieve a variety of symptoms.

Thus, in another aspect, the invention is directed to a method to treat undesirable endogenous conditions by applying to the skin of a subject in need of such treatment an effective amount of the concentrated filtrate of a *Basidiomycete* fungus culture described above or a pharmaceutical composition thereof.

In another aspect, the concentrate may be diluted for application to plants.

In still another aspect, the invention is directed to methods to culture *Basidiomycete* fungus so as to provide a culture filtrate useful in treating these endogenous conditions, and in preparing an agricultural supplement. Also disclosed are methods to process the filtrate to convert the retrieved filtrate to a form for dermal administration by concentrating the fluid to a BRIX value that maintains sterility.

In still another aspect, the invention is related to a pharmaceutical preparation which comprises the concentrated filtrate. The composition may be stored in a suitable application container, such as a dropping bottle.

MODES OF CARRYING OUT THE INVENTION

Figure 1:
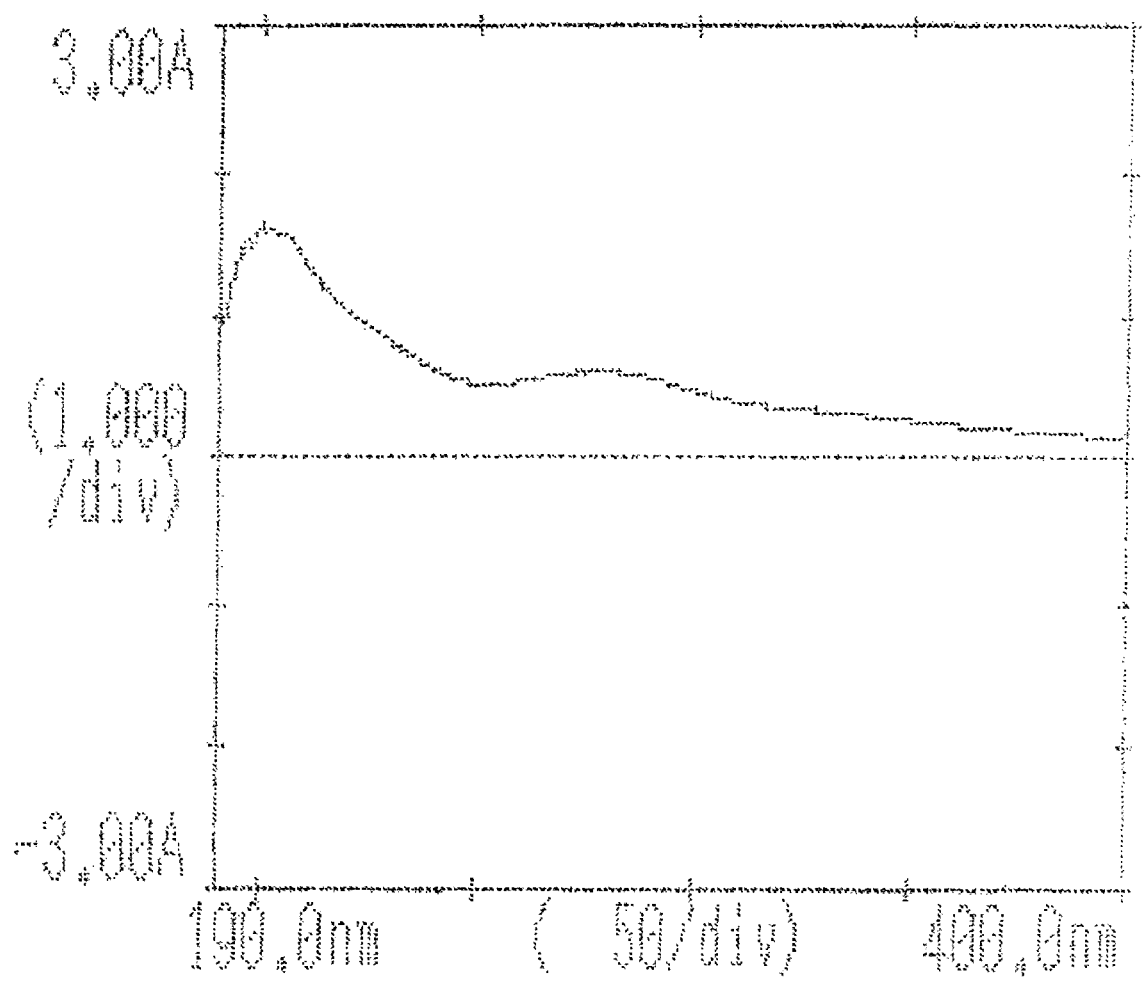
FIG. 1 shows a typical UV-visible spectrum of diluted concentrate suitable for dermal drops.

The invention is directed in part to methods of treating or ameliorating a variety of endogenous chronic conditions in human and other animal subjects. The methods employ a concentrated filtrate of a fungal spawn of *Basidiomycetes*. As a filtrate prior to concentration was originally disclosed in PCT publication WO 2004/006643 as containing plant growth modulators, the filtrate was designated "Liquid Compost Factor (LCF)." Simply "culture filtrate" or "CF" is defined herein as the optionally sterilized liquid portion of a fungal spawn culture which has been grown under specified conditions and in a medium that has high concentrations of available carbohydrate, i.e., a "culture filtrate." The compositions of the invention include concentrated forms of the sterilized filtrate from the fungal mycelial mat as well as dried forms thereof.

For optimal content of the compounds useful in the therapeutic dermal drops described herein, the fungal culture is incubated for extended periods—i.e. more than one year, or more than 2 years or for 3 years or more. As will be further described below, although the concentrate described generically above can be used either for topical application to treat chronic or related conditions in subjects, including human subjects, or can be used as a concentrated form of liquid compost factor (LCF), the precise conditions under which the culture is maintained and subsequently treated may determine optimal results for each application.

The CF obtained as described contains beneficial compounds which are secondary metabolites of the fungal culture. The production of these compounds is effected by appropriate culturing conditions and time, by appropriate medium composition, and by proper post-culture treatment. The medium must contain sufficient available carbohydrate and sufficient potassium ion to effect this production as well as the appropriate carotenoid precursors for metabolic production of these compounds. The potassium ion may occur naturally in culture nutrients. Molasses contains about 2%-6% potassium and is a preferred, environmentally acceptable source, although other sources such as bananas, potatoes, prunes, oranges, tomatoes, artichokes, squash, grapes, sunflower, spinach, seeds or almonds could be used as well. The final concentration of $K^+$ should be 0.01% to 0.7% wt/vol., preferably 0.05% to 0.5% wt/vol or 0.1% to 0.5% wt/vol.

In general, the higher the available carbohydrate content, the more efficient the production of the beneficial compounds; however, too high a concentration of carbohydrate in the form of sugars would unacceptably increase osmotic pressure and thus retard or eliminate growth of the fungus. Other factors which enhance the production of desirable compounds in the ultimate product include growth under conditions of aeration under conditions wherein the mycelial mat is left undisturbed and in the presence of light predominantly in the long wavelength portion of the visible spectrum. The lighting conditions suitable for culture are preferably those derived from U.S. Pat. No. 5,123,203, the contents of which are incorporated herein by reference. By addition of carotenoid pigments and reduction of $Ca^{+2}$ in the fruiting substrates, red light sources were found to be preferred especially if the concentrate is intended for topical animal use. Effective production is also enhanced by addition of carotenoid to the medium sufficient to produce a yellow, orange or red color. If, for example, pineapple juice is employed as a carbohydrate source, sufficient carotenoid precursor is inherently present.

It is known that calcium ion retards fruiting, because it interferes with potassium ion uptake in the fruiting bodies. However, controlling fruiting is desirable in order to encourage the production of secondary metabolites. This control can be effected by ensuring sufficient concentrations of carbon dioxide in the gas in contact with the culture. This can be accomplished by inhibiting the outflow of gases, such as by the use of cotton plugs.

While sufficient carotenoid to impart a yellow, orange or red color is appropriate regardless of the end use of the concentrate, it has been found that use of culture media that impart a bright yellow color is especially favored for the preparation of a concentrate for topical use in animals. Any source of carotenoid can be used, including synthetic carotenoids, but natural materials that contain yellow carotenoids are a more economical source. Thus, pineapple juice, orange juice, carrot juice, or other extracts that contain both available sugar and suitable carotenoids can be used in the medium.

On the other hand, if the concentrate is intended to be diluted for agricultural use, typically, higher yields of the desired compounds are obtained if the medium contains red carotenoids. Thus, in addition to synthetic red carotenoids, natural sources such as tomato juice, beet juice, cranberry juice, red watermelon, guava, red papaya, rose hips, blueberry extract, pomegranate concentrate and other extracts or juices that appear red are useful in the medium. White light sources are preferred also in this case.

While not intending to be bound by any theory, it is believed that the yellow carotenoids are enzymically converted to triterpenes by the culture but that red carotenoids do not undergo this conversion, and indeed may inhibit the conversion to triterpenes by the relevant enzyme. In any event, the culture filtrate can be skewed to be more suitable for preparation of the concentrate useful in topical application for animals by enhancing the levels of yellow carotenoid in the medium and also by increasing the time of culture. The filtrate can be skewed toward the preparation of concentrate for dilution to LCF by increasing the levels of red carotenoid in the medium and by harvesting the filtrate after only one year rather than extending the culture period to three or four years. Also, white light is preferred in this case.

The foregoing description is intended to describe how to optimize the presence of desired compounds for any particular use, but in all cases that fall within the rubric of the claimed concentrate, there are sufficient active components to perform either function.

The culture medium will contain an available sugar concentration corresponding to a content of 5-10% molasses. Although agricultural waste may be used to compose the medium, any source of suitable carbohydrates and other required nutrients, including carotenoid, could be used; some portion of the nutrients may be supplied by the fungal spawn itself which is prepared by culturing fungi in the presence of grains and other nutrients. Thus, the required sugar content of the medium can be supplied by syrups prepared from any source, including various fruits, corn syrup, sugar cane syrup, sugar beet syrup, molasses, and the like. Syrups prepared from other fruits, such as pineapple, orange, plum, grape, papaya and many others may also be used. It is preferred to use plant extracts as a source of nutrients in the medium.

The medium should have an available carbohydrate content which is higher than that typical for culturing of fungi. By "available carbohydrate" is meant carbohydrate energy sources which are metabolizeable by the fungal culture. Typical components of these available carbohydrates include sucrose, glucose, other simple sugars and disaccharides. Typically, the medium will contain at least 10% wt/vol available carbohydrate, preferably 12% wt/vol, more preferably 13% wt/vol, and even more preferably 15% wt/vol. Alternatively, the final concentration in the medium results in a BRIX reading of at least 5, or at least 12, or at least 16. High concentrations of available carbohydrate are highly preferred and, as stated above, are limited only by the necessity to avoid generating unacceptable osmotic pressure conditions. Since fungi are able to digest cellulose, enhancing the carbohydrate levels in the form of cellulose, or other carbohydrate which does not enhance osmotic pressure, may also be used.

It appears that optimal BRIX values for the culture medium are in the range of 12-15, although BRIX values of 5-16 are acceptable. In one typical culture, BRIX values above 19, e.g., 24 or 30, resulted in either very slow growth or no growth at all. At 19 BRIX, the mycelial covered the surface of the medium but in only a thin layer; at 11 BRIX and 8 BRIX a very good growth is achieved; BRIX values of about 5-6 are also effective.

In addition to the available carbohydrate as a carbon source, the medium must also contain other nutrients, notably a source of nitrogen and various cofactors. Typically, there is sufficient source of most of these nutrients in the fungal spawn used for an inoculum. However, it is important that the medium contain a concentration of carotenoid which is sufficient to provide a visible yellow, orange or red color. As noted above, the production of factors suitable for use in LCF is favored by higher concentrations of red carotenoids and the production of secondary metabolites useful for dermal application is favored by a higher proportion of yellow carotenoids.

If molasses is used as at least a portion of the source for available carbohydrate, the molasses itself supplies many vitamins and other nutrients required by the fungus. Syrups prepared from sugar cane are preferred to those prepared from sugar beet as these syrups provide a better source of nutrients. Other sources of desirable nutrients include the use of bananas for supply of potassium ion and papaya is also a helpful addition to the medium. Papaya contains carotenoids, sugars, and sulfur compounds. It is particularly high in fructose.

The starting pH of the medium should be somewhat acidic, preferably about 3-6. The pH drops somewhat over the long culturing period. Thus, acid-resistant culture vessels are preferred. Many of the juices that can be used in the medium are sufficiently acidic—if not, an organic acid, such as citric acid can supplement.

The medium is first sterilized, preferably by heating to a sufficient temperature for a sufficient time to remove any contaminating organisms. The decontaminated medium is then inoculated with a culture of fungus, i.e., a fungal spawn.

Any *Basidiomycete* fungus can be used in the invention provided it is adaptable to the culture techniques described herein. While a multiplicity of fungi have been described as able to produce various beneficial compounds, typically, this has not been the case as a means for commercial or practical production of these compounds. In addition, to applicants' knowledge, the skin penetration capability of culture filtrate from fungi has not been described, nor has preparation of a culture filtrate concentrate.

The culturing of fungi useable to obtain CF containing the desired components can be conducted in an efficient manner using readily available equipment. While stainless steel drums are useful, they are expensive and unless the stainless steel is especially formulated to resist corrosion, corrosion may occur during fermentation. Glass or plastic containers are therefore preferred. It has been found particularly convenient to culture the fungi in 40 or 55 gallon translucent plastic drums with just a cotton plug in the spigot. The insides of the drums or other containers are first decontaminated, for example with a dilute iodine solution, prior to use.

The fungi useful in the invention are *Basidiomycetes*—i.e., a class of fungi that coexist with, and depend for growth on, plants in nature. *Basidiomycetes* can be porous or gilled and preferred sources for the spawns cultured in the method of the invention are the porous fungi, in particular those of the family Polyporaceae. The Polyporaceae can generally be classified as constituting genera that are brown rot fungi or white rot fungi. The brown rot fungi degrade the white cellulose in wood on which they grow, thus leaving the brown lignin behind; the white rot fungi do the opposite—they degrade the lignin and leave the white cellulose behind. Thus, preferred fungi for use in the method of the invention are brown rot *Polyporus* fungi, and in particular those of the genera *Bridgeoporus, Ceriporia, Daedalea, Laetiporus, Oligoporus*, and *Pycnoporellus*.

Thus, the invention can employ, in the specific culture conditions required, various members of the *Basidiomycete* class, but preferably those that are in the *Polyporus* family and in particular those that are of the brown rot type.

One useful fungus employed in the invention is *Laetiporus*, especially *Laetiporus sulphureus*. *Laetiporus sulphureus* "Sulphur shelf" or "Chicken of the Woods" is a wound parasite of hardwood trees. It is commonly found in Hawaii on *Eucalyptus robusta*. Since this fungus lives in the heart wood of the tree, it is not noticeable on the outside of the tree. The fruiting body or mushroom appears as a sulphur or orange color bracket mushroom appearing every few years. The fungi feed on the heartwood and produce a cubical brown rot internally since the lignin is left after the cellulose and hemicellulose have been dissolved by enzymatic action. Tree death occurs many years after infection has started.

The concentrated fungal liquid culture of *L. sulphureus* has been shown herein to effect transdermal passage of beneficial compounds contained therein when applied in small amounts to the skin. As enzymes are destroyed by heating the fluid (as is done in preparing the CF for concentration), the beneficial compounds are heat stable at 100° C. They also are stable to conditions that effect concentration of the filtrate.

The nutrient medium for the fungus contains suitable components that are specifically tailored to the genus employed, but must always contain, of course, a source of carbon, a source of nitrogen, and relevant vitamins and cofactors. The spawn is produced by culturing for a suitable time period sufficient to provide sufficient fungal inoculum so that a mycelial mat will be formed in the culture medium of the invention. Typical time for formation of the spawn from an initial inoculation range from 5 days-100 days.

A commercially available liquid fungal spawn useful in the invention may be obtained from Kukui Spawn Co., formerly Maui Shiitake Trading Company, both of Maui.

The liquid spawn is then used to inoculate the culture medium for preparation of the CF. The inoculated culture medium is cultured without agitation in the presence of light predominantly in the long wavelength portion of the visible spectrum, at a temperature of 15-37° C., preferably about 20° C. for a sufficient time to generate the required levels of the desired compounds. Typically, these compounds are produced after 60 days of culture, but larger and more useful quantities are produced after one, two, three or four years or more of culturing the mycelial mat. The dermal drops are prepared from cultures of these or longer durations.

Although agitation of the inoculated culture medium is to be avoided in order to avoid disturbing the mycelial mat, aeration of the medium may be desired. This can be supplied, for example, by bubbling oxygen through the medium, or other means whereby the mycelial mat is left undisturbed. It has been found that sufficient oxygen is available even without bubbling air through the medium and simply permitting aeration to occur through interaction with the mycelial surface.

By "long wavelength portion of the visible spectrum" is meant light with a wavelength of approximately 500-800 nm, preferably 600-750 nm. Other wavelengths may be included, but the predominant wavelengths should be in the above range. Thus, as a percentage of total photons, the long wavelength portion should represent more than 50% of said photons.

As the culture matures, a mycelial mat will be grown, and the liquid portion of the culture can readily be removed aseptically when sufficient production of the desired components has occurred. Solids are removed from the harvested culture medium, either by filtration or alternatively by centrifugation or other known means to separate out solids. The filtration or other removal of solids does not require special equipment; use of paper towels, common filter paper, low-speed centrifugation, and the like is sufficient to remove portions of the culture which are sufficiently large to be visible as solids. The liquid portion is then subjected to heating to 100° C. and held for 10 minutes to denature unwanted enzymes. Membrane filtration could also be used to remove these proteins. The denatured proteins can be paper filtered or removed by centrifugation. The liquid portion is then subjected to suitable sterilization procedures, such as pasteurization and ultrafiltration, preferably pasteurization. "Sterilization" of the CF of the invention can be effected by a variety of means, such as ultrafiltration or inclusion of antibiotics or sanitizers such as Idophor.

The resulting sterilized CF is then simmered below boiling for 2-3 days to evaporate excess water or until the BRIX level reaches about 20 to about 30 or intermediate values. It will be noted that solutions with BRIX values of about 20 are self-sterilizing. This "CF concentrate" is the major and active component of the composition referred to herein as "dermal drops." If desired, higher BRIX values up to 60-65 can be achieved for reduction in volumes use in shipping. The BRIX value of the concentrate in the dermal drops of the invention, however, is typically 20-30 BRIX and the concentrate must be diluted to much lower BRIX values for application to agricultural crops.

The culture flask with the mycelial mat may, if desired, refilled with sterile, cool nutrient solution for preparation of additional CF. The second CF production takes less time than the first, since the mycelial mat has been established in the first run. The third and subsequent production runs are also shorter and may be continued until the culture vessel becomes contaminated.

Thus, the mycelial mat can be reused after removal of the medium for harvesting the CF. Typically, the medium can be removed through tubing from under the mat and replaced by new sterile medium. As typically the mat is broken during removal of the prior medium, the new sterile medium can simply re-poured into the container and the portions of the mat re-assemble and continue to grow.

As exemplified below, additional culture filtrate may optionally be gently squeezed out of the mycelial mat and treated as described above to obtain an additional yield. In addition, sludge that forms at the bottom of the culture vessel also contains culture filtrate within its matrix and this can be harvested by freezing to deplete the matrix and then obtaining additional yield from the sludge.

By "culture filtrate" (CF) is meant the liquid portion of the culture described. "Culture filtrate" is a commonly used term, despite the fact that recovery of this filtrate may not necessarily be effected by actual filtration. Indeed, in many of the cultures of the present invention, a mycelial mat is formed so that the culture filtrate may be removed by decanting or by siphoning. "Culture filtrate" thus refers simply to the liquid portion of the culture.

In all cases, the CF, whether obtained from the major liquid portion of the culture, from the liquid portion that is included within the mycelial mat, or from the sludge formed in the container, is treated similarly by denaturing and removing soluble proteins typically by heating to 100° F. for 10 minutes or comparable conditions that are sufficient to denature the protein but not destroy the active compounds, and then concentrated. The concentration step is conducted below the boiling temperature, preferably at 180-200° F. for about 2 or 3 days to 5 days; 6 days appears to be too long. During the concentration process, the dark brown liquid CF becomes a red cherry color which then turns brown again when exposed to air.

To prepare the concentrate useful in dermal drops, the concentration step is terminated after levels of 20-30 BRIX are achieved. However, further concentration may be effected up to 60-65 BRIX. At these high concentrations, precipitation of active compounds occurs, and this technique may be used as a method to purify these compounds.

Dermal Drops

The preferred concentrate for use in topical application is 20-30 BRIX and is optionally supplemented with other nutrients. The dermal drops may be applied topically to the skin of any animal, including humans. However, the dermal drops may also have veterinary uses for mammalian or avian subjects as well. Thus, the drops may be applied to household pets such as cats and dogs or livestock such as cows, pigs and sheep. Chickens and ducks may also be subjects. It may be necessary to expose the skin of these animals to apply the drops.

As noted above, the production of the active ingredients in dermal drops is favored by high concentrations of yellow carotenoid, relatively low concentrations of red carotenoid and longer duration of culture maintenance such as 3-4 years. As a quality control for assuring favorable outcomes, a UV-visible spectrum of the concentrate is taken. A 1:1,000 dilution is taken before the analysis is done, and a concentrate that shows high peaks is preferred for this application. A typical spectrum is shown in FIG. 1. UV-visible spectra with lower peaks at this dilution characterize concentrates more useful for agricultural applications.

The CF concentrate is optionally diluted slightly with extracts of edible mushrooms for administration. Typically, the final preparation will contain 80-100% of the LCF concentrate, including intervening percentages, and 20-0% of aqueous extracts of edible mushrooms, such as shiitake (*Lentinus edodes*) and/or black ear fungus (*Auricularia* sp). There appear to be effective concentrations of beneficial compounds in the resulting composition, including PPAR modulators such as dehydrotrametenolic acid.

As further described below, these dermal drops contain beneficial therapeutic compounds. In addition to this direct use, the dermal drops may also be supplemented with additional synthetic drugs to take advantage of the penetrating power of the dermal drops concentrate. Thus, such standard pharmaceuticals as the statins, such as simvastatin, atorvastatin, and the like, polyketide antimicrobials such as epothilone, erythromycin and the like, cytotoxic antitumor drugs derived from polyketides such as daunorubicin or doxorubicin, beta blockers, serotonin uptake inhibitors, or any of a wide variety of other prescription or non-prescription drugs can be combined with the dermal drops to effect topical application. The foregoing list is by no means exhaustive and is intended simply to state that any drug that is otherwise administered orally or by injection or by suppository could be reformulated in a topical formulation by including it in a dermal drop-based preparation. Typically, the additional drug will constitute 5-50% of the topical formulation, including all percentages between these limits.

The compounds contained in the CF and thus in the final dermal drop preparation exert a number of metabolic effects when applied topically through the skin. Only small amounts are required—typically 1-4 drops per day and 1-3 drops per individual application. The active ingredients are able to lower blood sugar levels in diabetic subjects, to reduce pain (unless the pain is caused by torn muscles), to increase stamina and mental clarity, to increase blood circulation and to have general physiologically favorable effects in animal subjects.

For muscle pain relief, the effects of application are felt in 5-10 minutes after the product is first rubbed into the skin. It is not necessary to apply the drops to the pain area; application to the arms or legs is suggested. Re-application may be necessary after about 4 or 5 hours.

For lowering sugar levels, effects are obtained within an hour to a maximum effect after two hours, though at low does longer times, e.g. overnight, may be required. In order for the drops to work, endogenous insulin must be present or must be administered to the subject. In general, for control of blood sugar, two applications per day is suggested with 1-4 drops being administered per application depending on the subject.

Because of the small dosage amounts required, the pharmaceutical composition that contains CF concentrate is generally designated "dermal drops." In one embodiment of the invention, the dermal drops of the invention are 90% CF concentrate with a BRIX value of 30 with 10% of water extract of *Auricularia* sp (black ear fungus) and *Lentinus edodes* (shiitake). It is believed the latter two components are not essential.

The dermal drops my be used to ameliorate the symptoms of diabetes of both Type 1 and Type 2 as well as treating Parkinson's and Alzheimer's diseases as these conditions may be affected by an accumulation of sugars in the brain. The dermal drops also reduce edema, reduce fatigue, reduce muscle pain from overworking and an aid in weight loss. Applying these drops will increase stamina and mental clarity and reduce caffeine usage. The dermal drops also reduce psoriasis, increase blood circulation and reduce tremors due to Parkinson's disease. The analgesic effects of dermal drops makes them useful in treating variability of indications including headaches, carpal tunnel syndrome, and the like. Dermal drops also have an antitumor effect, in particular with regard to leukemia and stomach cancer. Inflammation is also reduced, indicating that the dermal drops may be used to ameliorate the symptoms of arthritis.

As noted above, the dermal drops of the invention are effective to treat "endogenous conditions" in subjects. By "endogenous conditions" is meant conditions that result from metabolic imbalances which are either produced by inate metabolic aberrations or which may, ultimately, be caused by infection such as viral or bacterial or proteasomal infection. Some examples follow:

Diabetes mellitus is a group of metabolic diseases characterized by high levels of blood glucose (blood sugar). In a person with diabetes, the normal use of food for energy is disrupted because of defects in insulin production, insulin action, or both. Insulin is a hormone which assists with the uptake of glucose into the body's cells. When insulin defects are present, the normal pathway of energy production is disrupted and high blood glucose levels result.

National estimates regarding the number of people suffering from diabetes show that 20.8 million people of all ages or 7% of the population has diabetes. Of these 20.8 million people, 14.6 million have already been diagnosed with diabetes 6.2 million remain undiagnosed.

There are two major categories of diabetes—Type 1, or insulin-dependent diabetes mellitus (IDDM) also known as Juvenile diabetes and brittle diabetes. In this form of the disease, the β cells that normally produce insulin are not available or destroyed and administration of insulin is required for treatment. These subjects must be administered insulin as well as applying the dermal drops.

The other type of diabetes is non-insulin dependent diabetes (NIDDM) or insulin-independent or Type 2 diabetes. In this type, the β cells produce some insulin but not in sufficient amount or the insulin does not properly regulate glucose metabolism. This type can often be controlled by life-style factors or by stimulating the β cells to produce additional insulin.

Another important aspect of diabetes in the United States is the number of people who have pre-diabetes, which is a condition that raises the risk of developing Type 2 diabetes, heart disease, and stroke. The National Diabetes Fact Sheet 2005, states that people with pre-diabetes have blood glucose levels higher than normal but not high enough to be classified as diabetes. People with pre-diabetes have impaired fasting glucose (IFG) or impaired glucose tolerance (IGT). Some people have both IFG and IGT. IFG is a condition in which the fasting blood sugar level is 100 to 125 milligrams per deciliter (mg/dL) after and overnight fast. The level is higher than normal but not high enough to be classified as diabetes. IGT is a condition in which the blood sugar level is high (140 to 199 mg/dL) after a 20 hour oral glucose tolerance test, but is not high enough to be classified as diabetes. Statistics from the National Diabetes Fact Sheet 2005 indicate that pre-diabetes, IFG, and IGT are very significant in the United States. In a cross-section sample of U.S. adults aged 40-74 years tested from 1988 to 1994, 33.8% had IFG, 15.4% had IGT, and 40.1% had pre-diabetes (IGT or IFG or both). By applying these percentages to the entire U.S. population, in 2000, an estimated 35 million adults aged 40-74 had IFG, 16 million had IGT, and 41 million had pre-diabetes (there is and overlap between the IFG and IGT groups).

Arthritis comprises over 100 different diseases and conditions. The most common are osteoarthritis, gout, rheumatoid arthritis, and fibromyalgia. Common symptoms include pain, aching, stiffness, and swelling in or around the joints. Some forms of arthritis, such as rheumatoid arthritis and lupus, can affect multiple organs and cause widespread symptoms. Arthritis is one of the most prevalent chronic health problems and the nation's leading cause of disability among Americans over age 15. It limits everyday activities such as walking, dressing and bathing for many Americans. According to the Arthritis Foundation, in 2005, 66 million (nearly 1 in 3 adults) had arthritis. 42.7 Million have doctor-diagnosed arthritis and 23.2 million people live with chronic joint symptoms, but have not been diagnosed by a doctor. It has also been found that arthritis tends to affect more women than men as 25.9 million women have doctor-diagnosed arthritis compared to 16.8 million men. Arthritis affects people in all age groups including nearly 300,000 children.

Stroke, brain damage caused by a lack of blood flow to part of the brain. In order to perform its many functions and direct activities throughout the body—from walking to seeing to reasoning—the brain requires a constant supply of energy, provided by the oxygen and nutrients that are delivered by the flowing blood. If blood flow is restricted or cut off at any point between the heart and the brain, portions of the brain relying on blood from the obstructed blood vessel become deprived of oxygen. Brain cells are extremely sensitive to such oxygen deprivation, and if they are deprived of oxygen and nutrients for more than several minutes, they, in effect, starve to death. A stroke results in permanent damage to the brain tissue—and in many cases, permanent disability for the patient.

Stroke is the third leading cause of death in the United States. Over 160,000 people die each year from stroke in the United States. Stroke is also one of the leading causes of serious long-term disability. Someone suffers a stroke every 45 seconds, and every 3.1 minutes someone dies of a stroke. According to the American Heart Association, stroke cost almost $57 billion in both direct and indirect costs in 2005. According to the Centers for Disease Control and Prevention, about 700,000 strokes occur in the Untied States each year. About 500,000 of these are first or new strokes. About 200,000 occur in people who have already had a stroke before. Nearly three-quarters of all strokes occur in people over the age of 65, however strokes can and do occur at any age.

Parkinson disease is a brain disorder. It occurs when certain nerve cells (neurons) in a part of the brain die or become impaired. Marked by trembling of the arms and legs, muscular rigidity, and poor balance, Parkinson disease is slowly progressive, worsening over time. Eventually symptoms may cause problems with walking or talking and, in some people, difficulty thinking. Physicians do not know how to cure Parkinson disease, but drug therapy or surgery may alleviate some of the most troubling symptoms.

The National Parkinson Foundation based in Miami, Fla., estimates that 1.5 million people in the United States are affected with Parkinson disease, although estimates are difficult to make because symptoms of the disease are often mistaken for the normal effects of aging or are attributed to other diseases. It is estimated that 60,000 new cases of Parkinson disease are diagnosed in the United States every year. Parkinson disease occurs in people all over the world, with the incidence in men slightly higher than in women. People most commonly develop Parkinson disease around the age of 60, and the incidence rises with age. However, at least 10 percent of cases occur in people under age 40, and a rare form of the disease affects teenagers.

Carpal tunnel syndrome is a painful progressive condition caused by compression of a key nerve in the wrist. It occurs when the median nerve, which runs from the forearm into the hand, becomes pressed or squeezed at the wrist. Symptoms usually start gradually, with pain, weakness, or numbness in the hand and wrist, radiating up the arm. As symptoms worsen, people might feel tingling during the day, and decreased grip strength may make it difficult to form a fist, grasp small objects, or perform other manual tasks.

Carpal tunnel syndrome affects about three out of every 100 people in the United States, although some estimates place the number higher. It is one of the most common causes of partial disability—both temporary and permanent.

It is estimated that 22,280 Americans (13,400 men and 8,880 women) will be diagnosed with stomach cancer during 2006. There will be an estimated 11,430 (6,690 men and 4,740 women) deaths from this type of cancer in 2006. This is a disease that mostly affects older people. Two thirds of people diagnosed with stomach cancer are older than 65. The risk of developing stomach cancer in a person's lifetime is about 1 in 100.

Stomach cancer is much more common worldwide, particularly in less developed countries. It is the second-leading cause of cancer-related deaths in the world, with approximately 700,000 deaths in 2002.

An estimated 198,257 people in the United States are living with leukemia. An estimated 34,810 new cases of leukemia will be diagnosed in the United States this year.

Acute leukemia is a rapidly progressing disease that results in the accumulation of immature, functionless cells in the marrow and blood. The marrow often can no longer produce enough normal platelets, red blood cells and white blood cells. Anemia, a deficiency of red cells, develops in virtually all leukemia patients. The lack of normal white cells impairs the body's ability to fight infections. A shortage of platelets results in bruising and easy bleeding.

Chronic leukemia progresses more slowly and allows greater numbers of more mature, functional cells to be made.

The foregoing discussion emphasizes the importance of the availability of dermal drops to the human population; however, the utility of this medication is not limited to humans, but is also applicable to other animal subjects, including other primates, household pets, livestock, avian subjects, and even fish. In some cases, it will be necessary to prepare the dermal surface in order to permit effective administration—e.g., by shaving hair or removing feathers.

In addition to containing compounds that are physiologically active in a variety of contexts, the dermal drops are useful excipients for effecting skin penetration and allowing topical administration of compounds including those that may not ordinarily be administered transdermally. This is particularly helpful for individuals who have difficulty swallowing pills or capsules.

Agricultural Applications

The concentrate of the invention may also be used in the agricultural applications described in WO 2004/006643. As noted above, the concentrations of compounds useful in this application is optimized by enhancing the amount of red carotenoid in the culture medium and the use of relatively short culture times, i.e., less than 2-3 years. The concentrates useful in agriculture are generally characterized by lower peaks in the UV-visible spectrum obtained by diluting the concentrate to a level appropriate for application to crops. For example, if the BRIX value of the concentrate is 30, 1 oz diluted to 125 gallons would be appropriate. For higher or lower BRIX values, proportionally smaller or larger amounts of the concentrate would be used to provide 125 gallons of formulation, which would be sufficient for one acre of crop. However the dilution would also vary depending on the crop. The concentrate having a BRIX value of 30 or even higher (up to 60-65) all of which concentrations are self-sterilizing, can be a convenient way to supply these plant growth modulators. The concentrate will typically be diluted 1:1000, 1:5000, 1:10,000, 1:20,000, 1:50,000 or intervening values depending on the BRIX value, the mode of application and the intended use. For example, a 1:18,000 dilution of 30 BRIX is typically used for lettuce and a 1:9000 dilution of 30 BRIX for woody plants.

The metabolites contained in the concentrate, when suitably diluted and applied have been shown to increase the yield of tomatoes by a factor of 2, and of cabbage by a factor of 3 over shorter growing periods. It can also triple cucumber production, in particular when used with fertilizers with added calcium ion. Enhanced yields of cotton crops have also been demonstrated.

The diluted concentrate, like the LCF of the above-referenced PCT publication, has also been shown to elicit systemic acquired resistance in plants. Systemic acquired resistance is a resistance response in the overall plant that follows an earlier localized exposure to a pathogen. This type of resistance confers in response to a wide range of pathogens and is associated with a still incompletely described metabolic pathway.

The following examples are offered to illustrate but not to limit the invention.

EXAMPLE 1

Preparation of LCF Concentrate and Dermal Drops

Medium was prepared from:
20 gal of high-fiber pineapple juice retentate obtained from ultrafiltration,
1 gal of pineapple syrup,
20 gal of molasses water (5 gal of molasses mixed with 40 gals of water), and
5 gal of soft ripe-stage papaya purée, optionally including skin, seeds and pulp.

The total volume was then adjusted to 50 gal with additional retentate and/or molasses water. The components were mixed in an open plastic drum and transferred to stainless steel pots, brought to a boil, and held at 100° C. for at least 30 min. The hot slurry was transferred to a sanitized, white translucent, 40-55 gal plastic bioprocessing drum and cooled to room temperature. Cooling takes several days.

The cooled medium was inoculated with fungal starter culture (see below) under a laminar flow-hood and one or two sterilized cotton plugs were installed in the 55 gal drum. The drum was then incubated in an air-conditioned, lighted room for 3 years undisturbed. The lighting was supplied by Agro-lights or deluxe warm white light. Cool white light is not satisfactory. Although shorter time periods may be used, 3 years permits the desired metabolites to accumulate to satisfactory levels.

The fungal starter culture used in this Example was obtained from Kukui Spawn Co., formerly Maui Shiitake Trading Company, Hawaii. The entire 1 liter container of liquid spawn is added aseptically to the bioprocessing drum of cooled nutrient solution. Usually two bottles of spawn liquid culture is added per 50 gallon bioprocessing drum.

After incubation, the liquid portion of the culture was removed and filtered to remove solids. The filtered liquid was heated to 100° C. for 10 minutes to denature soluble proteins. The heated medium was then filtered and reheated to 100° C. for 30 minutes to pasteurize. The pasteurized product was simmered at 180 degrees F. for several days to evaporate excess liquid until the BRIX level reached about 30.

The CF concentrate was then mixed with an aqueous extract obtained by boiling black ear mushroom and shiitake mushrooms in water for one-half an hour and removing the filtrate to obtain dermal drops. The final composition was 90% CF concentrate and 10% of the mushroom extract.

EXAMPLE 2

Alternate Processing of Filtrate to Obtain Concentrate for Dermal Drops or Agricultural Use The fungal culture is prepared as in Example 1 and the mycelial mat (usually floating on the medium) is separated from the dark brown fluid. A brown thick sludge is also separated from bottom of bioreactor. This is fungal digested fruit pulp.

A. The recovered dark brown fluids are heated to boil for a few minutes then removed from the heat. This step changes the color to a dark red color and solubilized proteins (enzymes) denature and precipitate as a fine "snow" in the liquid. The heating also kills any live mushroom mycelia. The heated fluid is filtered through 4 layers of paper towels.

The filtered fluids are harvested and simmered at 180-200° F., which is hot enough for steam to be generated, but not boiling. The simmering liquids must be stirred intermittently. This low temperature keeps the antimicrobial compounds and triterpenoids intact. Fluids are simmered for about 24 to 36 hours to reduce the volume and raise the BRIX level to 30 BRIX. This time may vary due to the heat setting and initial BRIX level. (Initial BRIX reading will vary with the length of incubation time, 2 years may be 12 BRIX, 4 years may be 15 BRIX.) Longer simmering period (96 hours+) or continuous boiling will result in denaturing the antimicrobial compounds, triterpenoids and plant growth regulators, which is not desirable.

The concentrated fluids will appear as black cherry red, thick liquid. Higher BRIX 60-85) can be obtained but burning of the thick liquid is possible and this requires constant stirring and a double boiler to prevent scorching.

It is not necessary to follow the foregoing exactly—harvesting the filtrate may employ centrifugal filters instead of paper towels, using solid bowls or perforated bowls. Rather than concentrating by heating at atmospheric pressure, a low temperature/low pressure evaporator could be used.

B. To obtain additional CF for dermal drops, the dark brown sludge retrieved from the bottom of the culture is heated carefully to boil with constant stirring. This avoids an over-boil with hot sludge. Once boiling is achieved, the sludge is removed from the heat and filtered through 4 layers of paper towels. Recovered liquids are simmered to reduce the volume. Hot water is added to the filtered sludge to extract more dark red liquid. Hot water extraction is done 3 to 5 times. All recovered fluids are simmered. Filtered sludge still retains fluids held in a gelatin-like matrix. This filtered sludge is frozen for 3-4 days, then thawed. The freezing destroys the gelatin matrix and releases more dark red fluids.

Due to the fine sediments in the sludge-derived fluids a technique used in the wine business is used. "Fining" is a flocculation technique use to clarify wines. Due to the organic nature of the CF, chemical fining agents are not used. For every 5 gallons of recovered fluids, 6 well-beaten raw eggs are added and blended with the cool fluids. Fluid/egg mixture is heated and as the egg protein falls out of solution in the heating, it binds to the fine floating solids, and filtering clarifies the solution. Egg/fluids are filtered through 4 paper towels and the recovered fluids are simmered to the desired BRIX content. If the CF is to be used for agricultural purposes, solution clarity is important to prevent drip irrigation or spray heads from clogging.

In addition, the solids from the thawed filtered sludge are drained then placed in trays in drying ovens at 200° F. until dry. The dry filter cakes with filter papers are ground to a powder for use as a soil additive.

C. For further preparation of CF, the fungal mat is macerated in the drum with additional water using a motorized propeller blender. After several hours of blending, the mycelial mat sludge is harvested and filtered. Dark red fluids are recovered and added if desired to the simmering stocks of filtrate from paragraphs A and B. Hot water extraction is also used repeatedly.

D. For quality control, all recovered fluids are simmered to 30 BRIX. A 1:1,000 dilution of the 30 BRIX Syrup is taken and a UV/Vis absorbency curve is obtained for 190 nm to 400 nm. This is compared to standards. If the simmering steps were too long, the material may flat line. This may happen in the fluid recovery from the sludge or mycelial mat stage.

E. For preparation of dermal drops, concentrates with high peak displays in the UV/visible control described in paragraph D are selected. These are mixed with extracts of other edible mushrooms as described in Example 1 to obtain the final dermal drop preparation.

Notes:

All retained filtered solids (denatured enzymes, thawed drained sludge and cooked eggs) are dried and ground to a powder for later use.

The type of paper towel makes a difference due to retention rates and porosity. The best material is "Sparkle." Four layers retains the sludge but allows faster flow than other towels or Whatman paper filters. Filter cartridges clog fast with sludge. Centrifugal filters require several cleaning due to small capacity. Sludge binds to filter aid and renders it useless in vacuum filtration. Basically 4 paper towel layers in a colander is the best mode. A centrifugal filter is next best.

All pots and utensils are stainless steel. The recovered fluids have a pH of 2.5. Plastic equipment is also used. Aluminum and cast iron should be avoided.

EXAMPLE 3

Dermal Drops Composition

The finished product from Example 1 or 2 is put into dropper bottles for use by the subject. The directions provided are to use two drops as a skin rub on an arm or leg daily, but not to exceed four drops a day. The subject is instructed not to use the dermal drops on open skin cuts or sores, or to use it on the face or in the eyes or to ingest the material. Specifically, this is not a food. The length of time after application for the effect to be noticeable and duration of the effect vary with the symptom.

EXAMPLE 4

Treatment of Diabetes

A 36-year-old male with insulin-dependent diabetes applied four drops of dermal drops. After an hour from the time of application, the level of blood sugar dropped and stamina increased.

A 61-year-old male with insulin-dependent diabetes used two drops of dermal drops. After an hour from the time of application, a blood sugar drop was also noticed.

A 41-year-old male with insulin-dependent diabetes used four drops of dermal drops and experienced a diminution in blood sugar levels, after an hour from the time of application.

A 61-year-old female with insulin-dependent diabetes used four drops of dermal drops and experienced an improvement in circulation of blood.

A 70-year-old female with insulin-dependent diabetes administering four drops of dermal drops experienced a decrease in leg discoloration and an increase in blood circulation and stamina.

An 82-year-old male with insulin-independent diabetes administering four drops of dermal drops experienced increased blood circulation and increased stamina.

A 39-year-old male with insulin-independent diabetes using four drops of dermal drops experienced a decrease in blood sugar after two hours.

A 58-year-old male with insulin-independent diabetes administered four drops of dermal drops and experienced enhanced blood circulation and stamina.

A 62-year-old male with insulin-independent diabetes administered four drops of dermal drops and showed a decrease in blood sugar levels after an hour.

A 70-year-old male with insulin-independent diabetes applied four drops of dermal drops and experienced a diminution of blood sugar as well as higher energy level and clearer thinking. A numbness previously present in this individual's toes was also eliminated.

An 82-year-old male with insulin-dependent diabetes applying four drops of dermal drops experienced increases in blood circulation and stamina as well as energy and a decrease in muscle pain in his back and legs.

A 70-year-old female with insulin-dependent diabetes applied four drops of dermal drops experienced not only a decrease in leg discoloration but an increase in blood circulation and stamina, and a decrease in back pain.

A teacher who retired early due to diabetic problems, with insulin dependence, had blood sugar levels from 90 to 320 (normal is 80 to 120). After three days of dermal drops of 2 drops twice a day, her blood sugar is 70-100. Her attitude on life has changed, there is now hope that the disease is controllable with a longer life. She has been on the dermal drops for about 8 months.

EXAMPLE 5

Use of Dermal Drops to Treat Pain

A 87-year-old male used four drops of dermal drops and immediately experienced a decrease in muscle pain located in the arm.

A 45-year-old female using two drops of dermal drops experienced decreased muscle pain in her back adjacent the sciatic nerve. The subject also reported increased levels of energy and clearer thinking.

A 45-year-old male using four drops of dermal drops experienced decreased muscle pain in the back, knee and shoulder and reported increased energy level and clearer thinking.

A 72-year-old female using four drops of dermal drops experienced a decrease in muscle pain in the arms and overall as well as an increased energy level.

A 80-year-old male using four drops of dermal drops experienced decreased muscle pain all over his body as well as an increased energy level and clearer thinking.

A 50-year-old female using four drops of dermal drops experienced decreased muscle pain in her knees as well as an increased level of energy and clearer thinking.

A 50-year-old male using four drops of dermal drops experienced decreased muscle pain in his back and increased energy and clearer thinking.

A 75-year-old female using four drops of dermal drops experienced decreased muscle pain in her should and was able to sleep.

A 74-year-old male using two drops of dermal drops experienced decreased muscle pain in his shoulder.

A 60-year-old male using four drops of dermal drops experienced decreased muscle pain in his back as well as increased energy and clearer thinking.

A 62-year-old male using four drops of dermal drops experienced decreased muscle pain in his back, a decrease in swelling of his knees, as well as a higher energy level and clearer thinking.

A 44-year-old male using four drops of dermal drops experienced decreased shoulder pain as well as decrease in headaches and an increase in energy level and clearer thinking.

A 49-year-old female taking four drops of dermal drops experienced decreased muscle pain in the back and should and an increased energy level and clearer thinking.

A 58-year-old male using four drops of dermal drops experienced decreased muscle pain all over his body as well as increased energy and clearer thinking.

A 55-year-old male taking four drops of dermal drops experienced decreased muscle pain over his body and an increased energy level.

A 53-year-old male administered four drops of dermal drops experienced decreased muscle pain over his body and an increased energy level.

An 82-year-old female applying four drops of dermal drops experienced decreased pain in her legs and back.

A 41-year-old male applying only one drop of dermal drops experienced a decrease in headaches.

A 43-year-old male applying two drops of dermal drops experienced decreased muscle pain in his arm.

A 49-year-old female applying two drops of dermal drops experienced a decrease in muscle pain in her arm.

A 68-year-old male applying two drops of dermal drops experienced a decrease in muscle pain in his leg.

A 69-year-old male applying two drops of dermal drops experienced a decrease in muscle pain in his arm.

A 55-year-old male applying two drops of dermal drops experienced a decrease in muscle pain in his arm.

A 55-year-old male applying four drops of dermal drops experienced a decrease in muscle pain in his leg and back.

A 25-year-old male applying two drops of dermal drops experienced a decrease in muscle back pain.

A 54-year-old female applying two drops of dermal drops experienced a decrease in muscle pain in shoulder and arm.

A 70-year-old male applying four drops of dermal drops experienced a decrease in muscle pain in his arms.

A 59-year-old male applying two drops of dermal drops experienced a decrease in headaches as well as a decrease in skin discoloration.

EXAMPLE 6

Treatment of Carpal Tunnel Syndrome

A 41-year-old female applied four drops of dermal drops and noticed better mobility and decreased pain in the carpal tunnel condition from which she was suffering.

EXAMPLE 7

Treatment of Debilitation

An 85-year-old male, debilitated by surgeries for recurring skin cancer, applied several drops of dermal drop daily and regained sufficient energy to do farm and forestry work.

EXAMPLE 8

Treatment of Poor Eyesight

A 53-year-old male suffered loss of eyesight due to a stroke. After application of dermal drops, the patient was able to read smaller type than prior to application of the drops.

The invention claimed is:

1. A method to ameliorate the symptoms of a condition that is diabetes, pain or carpal tunnel syndrome in a mammalian subject which method comprises applying, topically to the skin of said subject, a culture filtrate
wherein, said filtrate is from a *Basidiomycetes* fungal culture that has been cultured for at least 1 year in a medium containing at least 10% available carbohydrate and a BRIX value of 5-16, that contains 0.01-0.7% wt/vol potassium ion and sufficient carotenoid compounds to impart a yellow, orange or red color, and wherein said culture is grown in the presence of long wavelength or white light, and in the substantial absence of agitation, and wherein said filtrate is the liquid portion of said culture and from which proteins have been denatured and removed, and wherein said filtrate is concentrated to at least a BRIX value of 20, or a pharmaceutical composition thereof.

2. The method of claim 1, that has a BRIX value of at least 30.

3. The method of claim 2, wherein said concentrate has a BRIX value of at least 60.

4. The method of claim 1, wherein said medium comprises molasses and/or pineapple or papaya syrup or juice.

5. The method of claim 1, wherein the culture has been cultured for at least 3 years.

6. The method of claim 1, wherein the *Basidiomycete* is a *Polyporus* fungus.

7. The method of claim 6, wherein the *Polyporus* is a *Laetiporus*.

8. The method of claim 1 wherein the concentrate is in admixture with an edible mushroom extract.

9. The method of claim 1 wherein the mammalian subject is human.

10. The method of claim 9 wherein the condition is diabetes.

11. The method of claim 9 wherein the condition is pain.

* * * * *